(12) United States Patent
Conlon et al.

(10) Patent No.: US 6,383,197 B1
(45) Date of Patent: May 7, 2002

(54) SELF DISENGAGING ANTI-BACKUP MECHANISM FOR SPECIMEN RETRIEVAL BAG DEPLOYMENT

(75) Inventors: Sean P. Conlon, Loveland; Thomas A. Gilker, Cincinnati, both of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/896,051

(22) Filed: Jun. 29, 2001

(51) Int. Cl.[7] .............................................. A61B 17/24
(52) U.S. Cl. ....................... 606/114; 606/110; 606/127; 600/37
(58) Field of Search .................. 606/110, 111, 606/112, 113, 114, 115, 127, 200; 600/37

(56) References Cited

U.S. PATENT DOCUMENTS

| 2,036,998 | A | * | 4/1936 | Brown |
| 5,465,731 | A | | 11/1995 | Bell et al. |
| 5,480,404 | A | | 1/1996 | Kammerer et al. |
| 5,643,283 | A | * | 7/1997 | Younker |
| 5,647,372 | A | | 7/1997 | Tovey et al. |
| 5,971,995 | A | | 10/1999 | Rousseau |
| 6,162,209 | A | * | 12/2000 | Gobron et al. |

\* cited by examiner

*Primary Examiner*—Pedro Philogene
(74) *Attorney, Agent, or Firm*—Dean L. Garner (57) ABSTRACT

A surgical instrument for retrieving tissue from a patient. The instrument includes an elongated support tube having a proximal end and a distal end, and an elongated inner rod slidably and coaxially disposed within the support tube. The rod has a removable pouch attached thereto, wherein the pouch is initially disposed within the support tube, and wherein distal movement of the rod ejects the pouch from the tube. The instrument further includes a mechanism engaging the rod such that after the rod has initially been moved distally, the mechanism prevents proximal motion of the rod. The mechanism disengaging upon total ejection of the bag from the tube, and thereafter allows proximal and distal movement of the rod.

10 Claims, 9 Drawing Sheets

SELF DISENGAGING ANTI-BACKUP MECHANISM FOR SPECIMEN RETRIEVAL BAG DEPLOYMENT

FIELD OF THE INVENTION

The present invention relates, in general, to surgical instruments for retrieving tissue and, more particularly, to endoscopic surgical instruments such as pouches or specimen retrieval bags for the removal of tissue through a small incision.

BACKGROUND OF THE INVENTION

Endoscopic surgery is a procedure wherein surgery is performed through a series of small openings or incisions in a patient. This type of surgery reduces or eliminates the need for large incisions and has changed some of the major open surgical procedures such as gall bladder removal to simple outpatient surgery. Consequently, the patient's recovery time has changed from weeks to days. These types of surgeries can be used for repairing defects or for the removal of diseased tissue or organs from areas of the body such as the abdominal cavity.

Of interest is the removal or excision of biological material or tissue from the body through a small opening such as an incision, a small natural orifice, or through a small diameter Laparoscopic access port such as a trocar. Tissue can have many types or forms but fall into three general categories: firm tissue such as muscle and solid tumors, soft tissues such as liver, and fluid filled tissues such as a cyst, a gall bladder, a spleen, or an inflamed appendix. Some tissue can be a mix of multiple categories. For example, an inflamed gall bladder can be a mix of hardened gallstones, fluids such as bile and pus, and an outer covering of firm tissue.

One challenge that exists with minimally invasive surgery is the removal of the excised tissue through the small opening. A time-honored solution is the manual cutting of the large tissue mass into small pieces that can fit through the opening. However, with this process fragments of tissue can be dropped and fluids can be spilled into the body cavity. This can cause complications if the excised tissue is cancerous or infected such as the seeding and re-spreading of cancer, or the spreading of an inflammation to healthy tissue.

In answer to the above challenges, surgical pouches or specimen retrieval bags were developed. The specimen retrieval bags are placed into an inner cavity of the body, the bags are opened, and the diseased tissue is placed within. The specimen retrieval bags are then closed to prevent the migration of tissue and fluids from the bag into the inner cavity of the body. After placing diseased tissue into the open specimen retrieval bag, the bag is closed and pulled from the opening in the patient. Drawstrings are typically used to close the specimen retrieval bag in the body and to draw the bag out of the opening in the body.

The small opening has forced several interesting design challenges to the makers of the specimen retrieval pouches. That is, the specimen retrieval pouches must be tightly rolled up or constrained to fit into the small opening within the patient, and fully opened or unfurled when deployed within the patient. To accomplish the above goals, a surgical deployment instrument was created. The surgical deployment instrument contains a tightly rolled or constrained specimen retrieval bag and a deployment mechanism that ejects and opens the bag from the distal end of the instrument. The surgeon activates the deployment mechanism by pushing on a deployment lever once the specimen retrieval bag is within the patient. Metallic spring arms are generally used to push the tightly rolled bag from the surgical deployment instrument and to spread open the opening of the bag. The excised tissue is placed into the open specimen retrieval bag, and the bag is closed by simultaneously detaching the bag from the spring arms and closing the opening of the bag with a drawstring. The spring arms are withdrawn back into the surgical deployment device by pulling the deployment lever back out of the surgical deployment instrument. The captured tissue is removed from the opening within the patient by pulling on the drawstrings to withdraw the specimen retrieval bag from the patient. Surgical instruments of this type are well known in the art and are described in U.S. Pat. No. 5,465,731 by Bell et al. , in U.S. Pat. No. 5,480,404 by Kammerer et al. , and in U.S. Pat. No. 5,647,372 by Tovey et al. which are incorporated herein by reference.

Specimen retrieval instruments have a specimen retrieval bag that is used to hold excised tissue. The specimen retrieval bags are generally held in an elongated support tube in a constrained condition. The specimen retrieval bag is inserted into the patient in the constrained state and the surgical retrieval instrument is fired to eject the bag from the elongated support tube and deploy it in an open state. Excised tissue is inserted into the open specimen retrieval bag and the bag is closed and detached from the specimen retrieval instrument. The fired specimen retrieval instrument and filled specimen retrieval bags are removed from the patient separately. Specimen retrieval instruments are well known in the art such as those described by Kammerer et al. in U.S. Pat. No. 5,480,404 and by Rousseau in U.S. Pat. No. 5,971,995, both of which are hereby incorporated by reference.

Whereas the above specimen retrieval bags and surgical deployment mechanisms worked well, in some cases, a surgeon could inadvertently partially activate the bag deployment mechanism and partially deploy the bag from the instrument. When the surgeon attempted to correct the mistake by de-activating the deployment mechanism, the bag could be partially detached from the metallic arms and fail to open properly. The partially opened bag, in some cases, was unusable and could require a replacement surgical instrument. To address this issue, motion control mechanisms or one way ratchet mechanisms can be incorporated with the surgical deployment instrument. Dual one way ratchet mechanisms are taught in U.S. Pat. No. 5,971,995 by Rousseau, each ratchet mechanism being fully engaged at all times. One ratchet mechanism limits proximal motion and one ratchet mechanism limits distal motion. Three nested and telescoping elements are provided, with two elements, one of which is the deployment lever, moving into the instrument to deploy the bag and one element, the deployment lever, moving out of the instrument to close and release the specimen retrieval bag. One ratchet mechanism limits travel of one of the two elements moving into the instrument and the second ratchet mechanism limits movement of the deployment lever moving out of the instrument. However, the dual ratchet mechanisms of the Rousseau device cannot prevent the surgeon from partially inserting the deployment lever and partially withdrawing the deployment lever. These actions can partially deploy the specimen retrieval bag from the surgical instrument.

What is needed is a simple low cost surgical deployment instrument that offers all of the advantages listed above and overcomes the needs described above. Thus, it would be advantageous to provide an improved simple motion control mechanism or ratchet mechanism that prevents the partial deployment of the specimen retrieval bag. . Presently, there are no known surgical deployment instruments that can provide the surgeon with the improvements and benefits described above.

SUMMARY OF THE INVENTION

In accordance with the present invention, there is provided a surgical instrument for retrieving tissue from a patient. The instrument includes an elongated support tube having a proximal end and a distal end, and an elongated inner rod slidably and coaxially disposed within the support tube. The rod has a removable pouch attached thereto, wherein the pouch is initially disposed within the support tube, and wherein distal movement of the rod ejects the pouch from the tube. The instrument further includes a mechanism engaging the rod such that after the rod has initially been moved distally, the mechanism prevents proximal motion of the rod. The mechanism disengaging upon total ejection of the bag from the tube, and thereafter allows proximal and distal movement of the rod.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
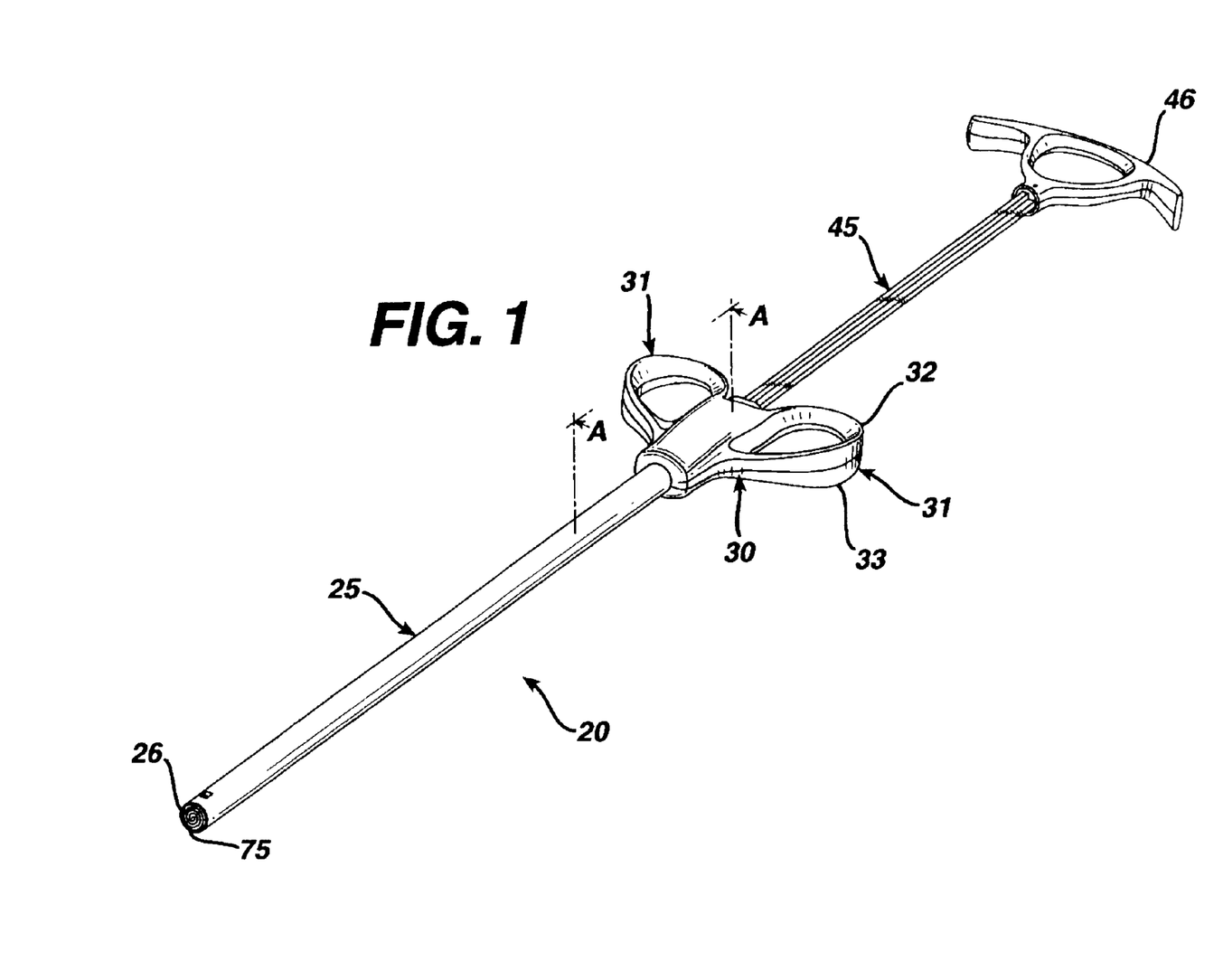
FIG. 1 illustrates an isometric view of an un-actuated specimen retrieval instrument with a push-pull rod extending proximally from a handle, the handle is located at a proximal end of a support tube and an improved specimen retrieval bag is constrained within a distal end of the support tube.

Referring now to the Figures wherein like numerals indicate the same element throughout the views, there is shown in FIG. 1 an isometric view of an un-actuated specimen retrieval instrument 20 ready for insertion into a patient. The specimen retrieval instrument 20 has an elongated support tube 25 with a handle 30 at a proximal end. Handle 30 has an upper half 32 and a lower half 33 fixedly attached to the elongated support tube 25. A pair of opposed finger loops 31 extend from the handle 30, and an unobstructed passageway 26 extends through the support tube 25 and handle 30. A push/pull rod 45 is slidingly located within the passageway 26 and has a thumb ring 46 at a proximal end and a pair of spring arms at a distal end. An improved specimen retrieval bag 75 is attached to a distal end of the push/pull rod 45 and is shown constrained within the passageway 26 at the distal end of the support tube 25.

Figure 2:
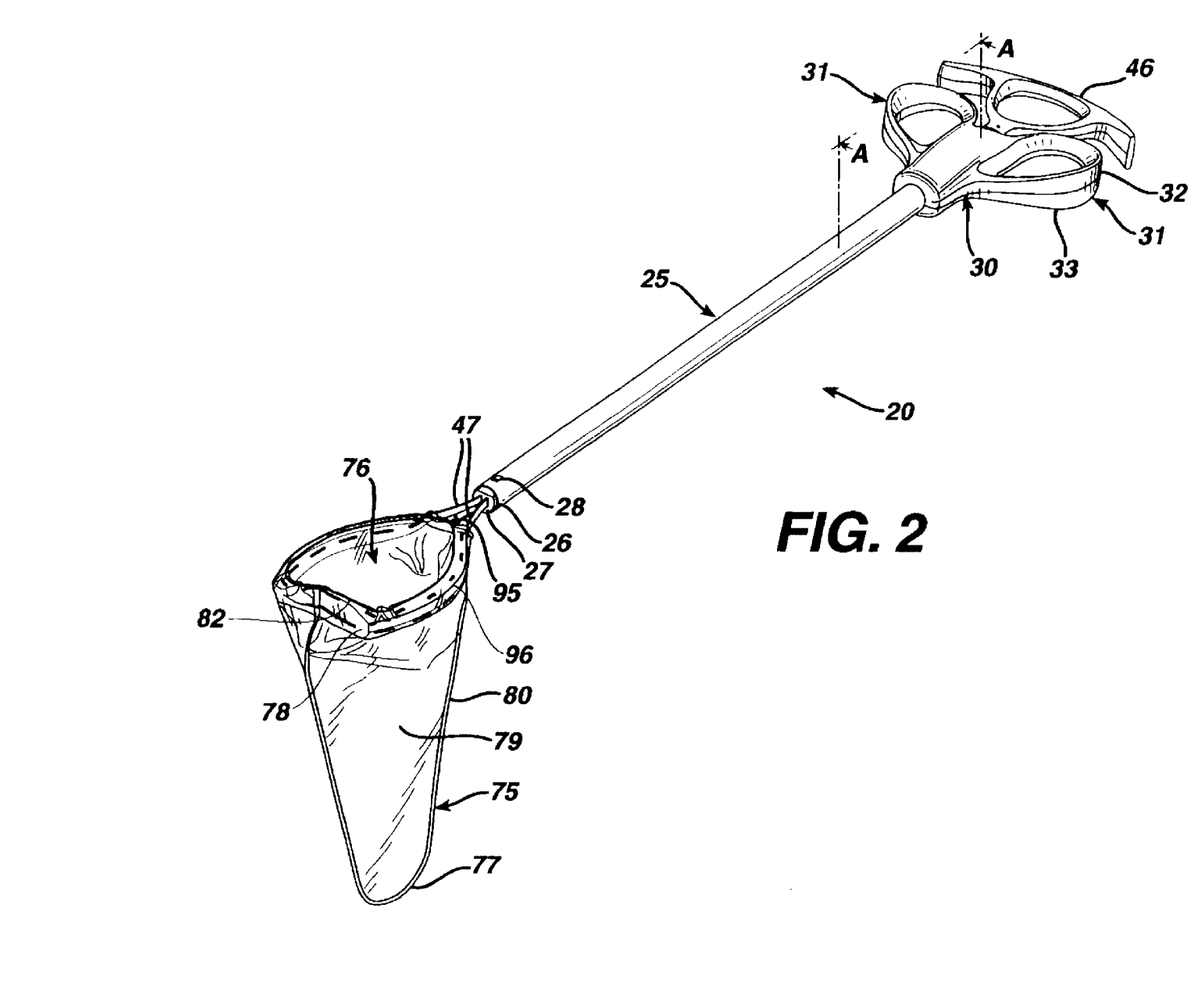
FIG. 2 illustrates an isometric view of an actuated specimen retrieval instrument of FIG. 1, the push/pull rod is shown fully inserted into the handle and support tube to deploy the improved specimen retrieval bag from the support tube.

FIG. 2 is an isometric view of the improved specimen retrieval instrument 20 after the instrument has been actuated to deploy the improved specimen retrieval bag 75 from the distal end of the support tube 25. The push/pull rod 45 has been fully inserted into the specimen retrieval instrument 20 and has pushed the improved specimen retrieval bag 75 from the distal end of the support tube 25 and locked a cinching plug 27 into a notch 28 in the support tube 25. A pair of opposed spring arms 47 releasably attaches improved specimen retrieval bag 75 to the push/pull rod 45. A closure string 95 is removably attached to the median of push/pull rod 45 and extends distally from an opening (not shown) within the cinching plug 27. Closure string 95 terminates in a captivated closeable noose 96 extending around the periphery of the open end 76 of the improved specimen retrieval bag 75. A slipknot 97 is used on the noose 96 so it can be closed as the push/pull rod 45 is pulled distally. Slipknot 97 resides in contact (not shown) with the cinching plug 27 just below the spring arms 47. Spring arms 47 spread open as they are released from the support tube 25 into a "Y" shape to open an open end 76 of the improved specimen retrieval bag 75. Spring arms are retained within channels 78 that are formed within each side of the improved specimen retrieval bag 75. Once the specimen retrieval bag is fully deployed, the one way ratchet mechanism 55 is permanently disengaged. Withdrawal of the unlocked push/pull rod 45 into the support tube 25 simultaneously withdraws the spring arms 47 from the channels 78 and closes the noose 96 to both disengage the improved specimen retrieval bag 75 from the end of the specimen retrieval instrument 20 and to close it. Spring arms 47 can be formed from a spring material such as stainless steel, nitinol, steel spring alloys, copper spring alloys, or any other material that can be stored in a deformed shape and return to an initial or near initial shape when released An improved motion limiting mechanism or one way ratchet mechanism 55 of the present invention (FIG. 6) is located within the handle 30 and operably engages with the push/pull rod 45. One way ratchet mechanism 55 operates only during the deployment of the improved specimen retrieval bag 75 from the elongated support tube 25. One way ratchet mechanism 55 slips during initial insertion of the push/pull rod 45 (to deploy the improved specimen retrieval bag 75) and locks if the attempt is made to withdraw the push/pull rod 45 during the initial deployment stroke. Once the improved specimen retrieval bag 75 is fully deployed from the end of the support tube 25, the one way ratchet mechanism 55 of the present invention permanently disengages and provides unrestricted proximal and distal movement of the push/pull rod 45.

Figure 5:
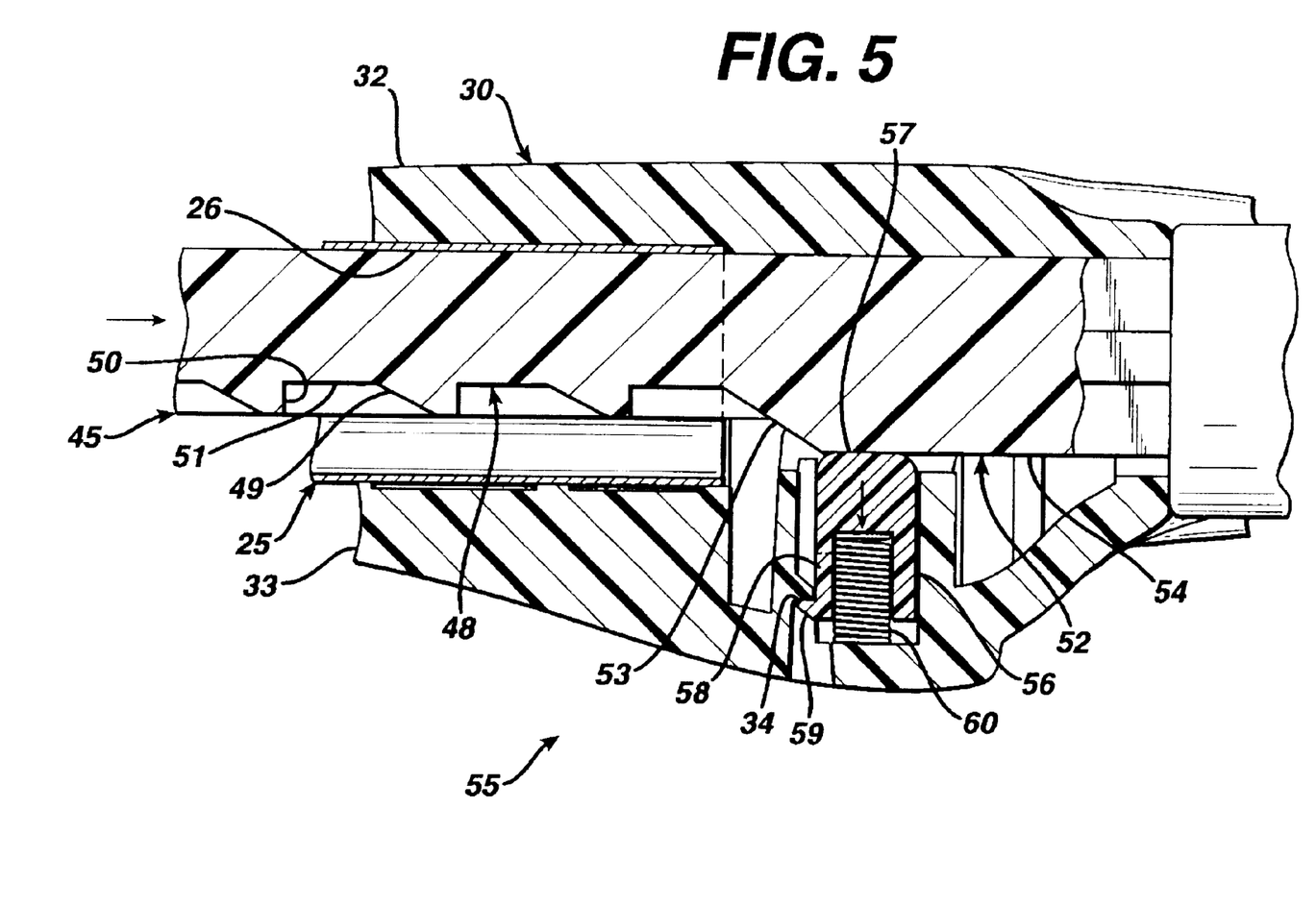
FIG. 5 illustrates a cross-sectional view of the improved one way ratchet mechanism of the present invention when the push/pull rod is fully inserted into the support tube as shown in FIG. 2. to permanently disengage the one way ratchet mechanism by pushing the spring loaded bullet downwardly to lockingly engage with the handle.
Figure 6:
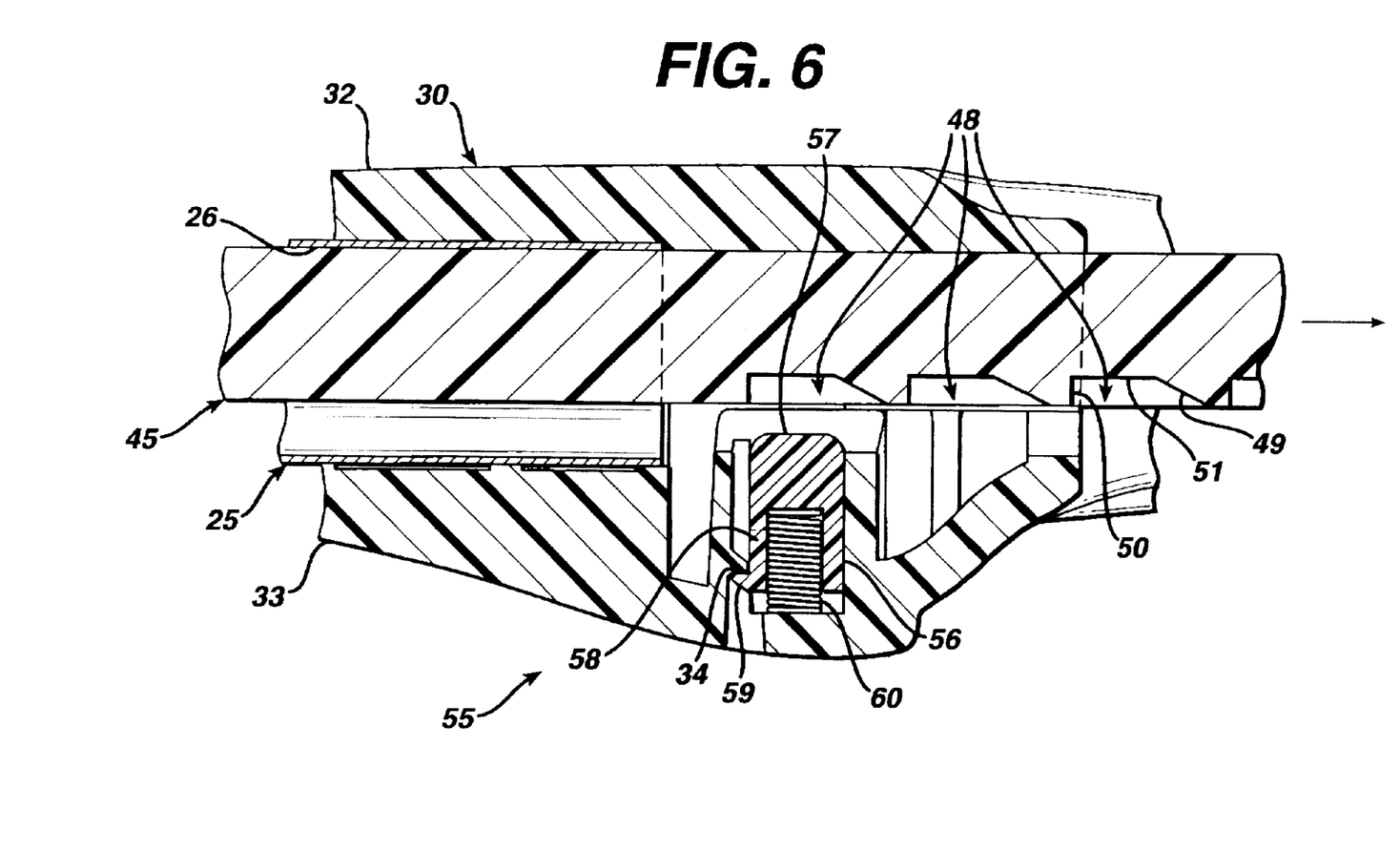
FIG. 6 illustrates a cross-sectional view of the improved one way ratchet mechanism of the present invention after the push pull rod has been pulled out of the support tube to release and close the specimen retrieval bag showing the spring loaded bullet remaining locked in the downward position and the one way ratchet mechanism permanently disengaged.

The one way ratchet mechanism 55 described above is only active during the push stroke (to deploy the improved specimen retrieval bag 75) to prevent a surgeon from partially deploying the improved specimen retrieval bag 75 and then partially withdrawing the spring arms 47 from the improved specimen retrieval bag 75. The one way ratchet mechanism 55 is primarily located within the lower half 33 of the handle 30 (FIG. 2) and is shown in FIGS. 4–6.

Figure 3:
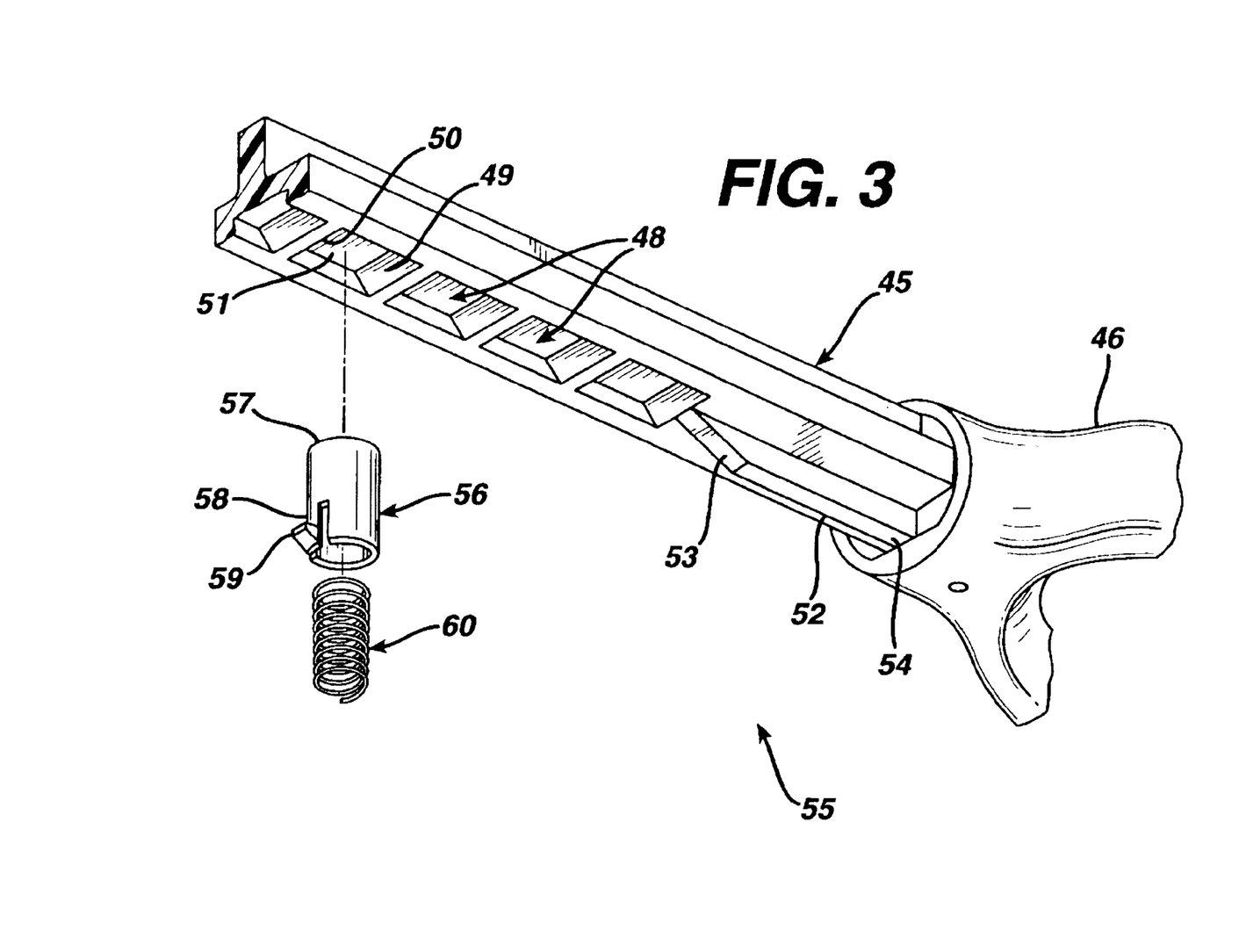
FIG. 3 illustrates an exploded isometric view of the active elements of the improved ratchet mechanism of the present invention.

FIG. 3 shows an exploded view of the active elements that make up the one way ratchet mechanism 55. One way ratchet mechanism 55 consists of a spring 60, a male feature or bullet 56 and the push/pull rod 45. Spring 60 normally pushes bullet 56 upwardly into operative engagement with a series of female features or pockets 48 equally spaced longitudinally along the bottom (as shown in FIGS. 1 and 2) of the push/pull rod 45. Pockets 48 interact with the bullet 56 to produce the desired one way ratchet action. Pockets 48 have an angled pocket ramp 49 on the proximal side, a vertical pocket flat 50 on the distal side, and a pocket floor 51. A locking blade 52 is located next to the thumb ring 46 at the distal end of the push/pull rod 45 and has a locking ramp 53 and a locking flat 54. In FIG. 3, the proximal end of push/pull rod 45 is shown and thumb ring 46 is sectioned.

Figure 4:
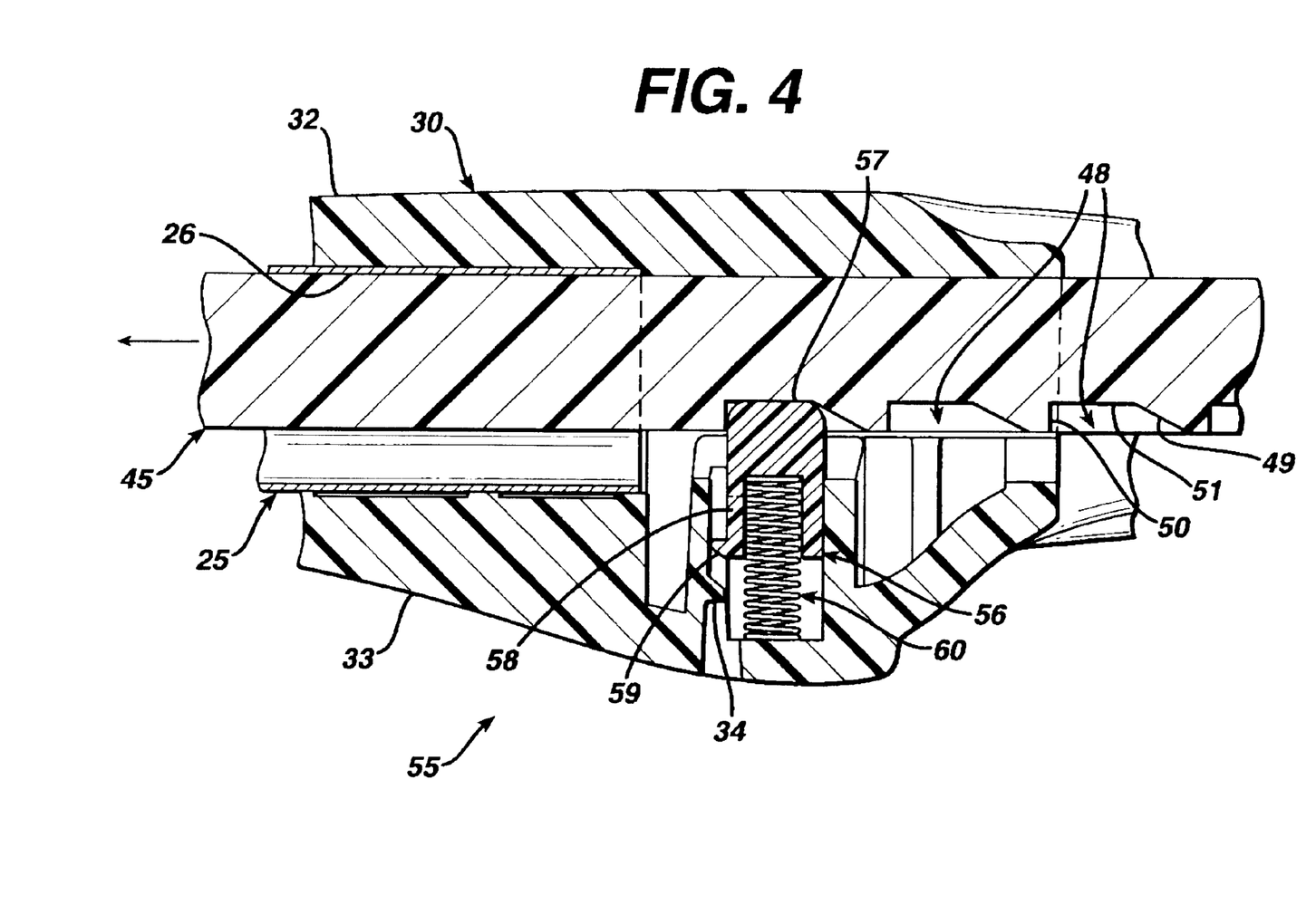
FIG. 4 illustrates a cross-sectional view of the improved one way ratchet mechanism of the present invention when the push pull rod is in the un-actuated position of FIG. 1 and a one way ratchet on the push/pull rod is actively engaged with a spring-loaded bullet to limit the direction of motion of the push pull rod to that shown by the arrow.

FIG. 4 is a cross-section of the assembled one way ratchet mechanism 55 within handle 30 when the push/pull rod 45 is fully extending from the handle 30 and ready to deploy the constrained improved specimen retrieval bag 75 from the distal end of the support tube 25 (FIG. 1). The engagement end 57 of the bullet 56 is being pressed against the pocket floor 51 by spring 60. The push/pull rod 45 is prevented from being pulled out (to the right in FIGS. 4–6) by the contact of the pocket flat 50 with the bullet 56.

Push/pull rod 45 is free to move distally (arrow direction) to deploy the improved specimen retrieval bag 75. Distal movement of the push/pull rod 45 brings the bullet 56 into contact with the pocket ramp 49 and bullet 56 moves downwardly as the ramp moves distally. As distal movement of push/pull rod 45 continues bullet 56 pops into the adjacent pocket 48. Any attempt to move the push/pull rod 45 proximally results in the bullet 56 contacting the locking ledge 34 of the pocket 48 (in which the bullet 56 resides) and prevents the proximal motion. Distal motion of push/pull rod 45 is not restricted.

FIG. 5 shows a cross-section of the assembled one way ratchet mechanism 55 when the push/pull rod 45 is fully inserted (see arrow) into specimen retrieval instrument 20. Improved specimen retrieval bag 75 is fully deployed from the distal end of the support tube 25 (FIG. 2) by this action. As shown, the bullet 56 has traversed all of the pockets 48 within the push pull rod 45 and has been pushed downwardly to the lowest position by the locking ramp 53 with the engagement end 57 of the bullet 56 resting on the locking flat 54. In this locked position, the hook 59 on deflectable locking arm 58 is retained or locked onto the locking ledge 34 of the lower half 33 of handle 30. When push/pull rod 45 is moved proximally (arrow direction), the locking blade 52 moves away from the bullet 56 and the locking engagement between hook 59 and locking ledge 34 holds the bullet 56 at the locked position. With the bullet 56 in the locked position, the bullet 56 can no longer interface with the pockets 48 and the one way ratchet mechanism 55 is permanently disengaged. With the bullet 56 in the locked position, the push/pull rod 45 is free to move in either direction.

FIG. 6 illustrates a cross-sectional view of the improved one way ratchet mechanism 55 of the present invention after the push pull rod 45 has been pulled out of the support tube 25 (see arrow) to release and close the improved specimen retrieval bag 75. The push/pull rod is in the same position as shown in FIG. 4, but bullet 56 is in the locked position, and the one way ratchet mechanism is permanently disengaged.

Figure 7:
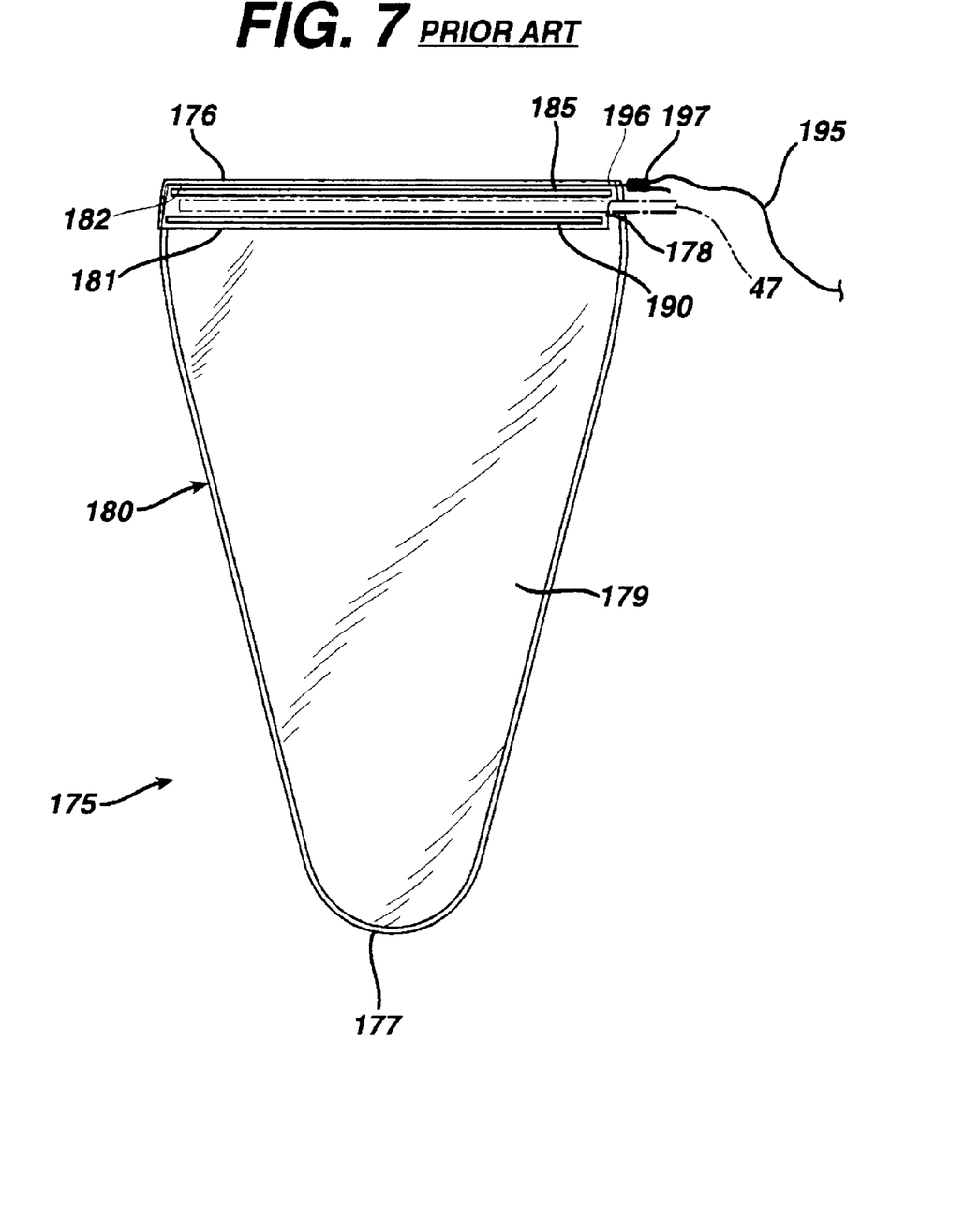
FIG. 7 illustrates a side view of a prior art specimen retrieval bag illustrating the two continuous lines of heat staking located under a closure noose.

Specimen retrieval bags are well known in the art for the reception and removal of tissue from the body. A prior art retrieval bag 175 is shown in FIG. 7 and has an open end 176, a closed end 177 and a closure mechanism such as closure string 195 captured around the open end 176. Closure string 195 is formed into a noose 196 by a slipknot 197. The prior art retrieval bag 175 is generally formed from a pair of opposed walls 179, each of which are cut from at least one layer of elastomeric or polymeric material. Walls 179 are constructed from at least one layer of an elastomeric or polymeric material such as but not limited to Polyurethane, Polyethylene, Polypropelene, Silicone, Vinyl, or Teflon. The walls 179 can be cut at an angle to produce a tapered retrieval bag that.

Multiple layer construction of the walls 179 are common and can incorporate flexible metal meshes, thermoformed plastic meshes, fabrics, or Kevlar for reinforcement. As shown, a pair of identical walls 179 are cut from flat sheets of Polyurethane into a desired shape with sides 180 tapered as shown to facilitate removal from the patient. The opposed pair of walls 179 are aligned together and attached together along the sides 180 and closed end 177 by gluing, heat welding, or ultrasonically welding to form a bag.

The closure string 195 is captured at the open end 176 of the prior art retrieval bag 175 by first folding over a portion of the open end of wall 179 to create a fold wall 181 in contact with the exterior of the wall 179 of the bag. Circular closure noose 196 of the closure string 195 is then placed around the prior art retrieval bag 175 and slid up into a crotch 182 of the fold between the interior surface of the fold wall 181 and the exterior surface of the bag wall 179. Alternately, a number of other closure mechanisms can be used such as a belt or a cable tie. The interior surface of the fold wall 181 is then attached to the exterior surface of the bag wall 179 in a continuous line, henceforth referred to as first continuous weld 185, located just below the closure noose 196 to capture the closure noose 196. Any one of the attachment methods listed above can form the continuous weld but generally heat staking is used. Heat staking uses a combination of heat and pressure to weld two layers of wall 179 together. This process can emboss or raise a rib of material from the surface of the wall 179. Care must be taken to ensure that the as first continuous weld 185 is present on each side of the prior art retrieval bag 175, that the process does not weld the bag closed, and that the noose 196 slides freely within. The first continuous weld 185 slidingly captures the closure noose 196 within the crotch of prior art retrieval bag 175 and enables the closure string 195 to move as closure noose 196 constricts. A second continuous weld line 190 is placed below the first continuous weld line 185 on both sides of the bag to create channels 178 therebetween for the reception of the spring arms 47 (shown as dashed lines).

Figure 8:
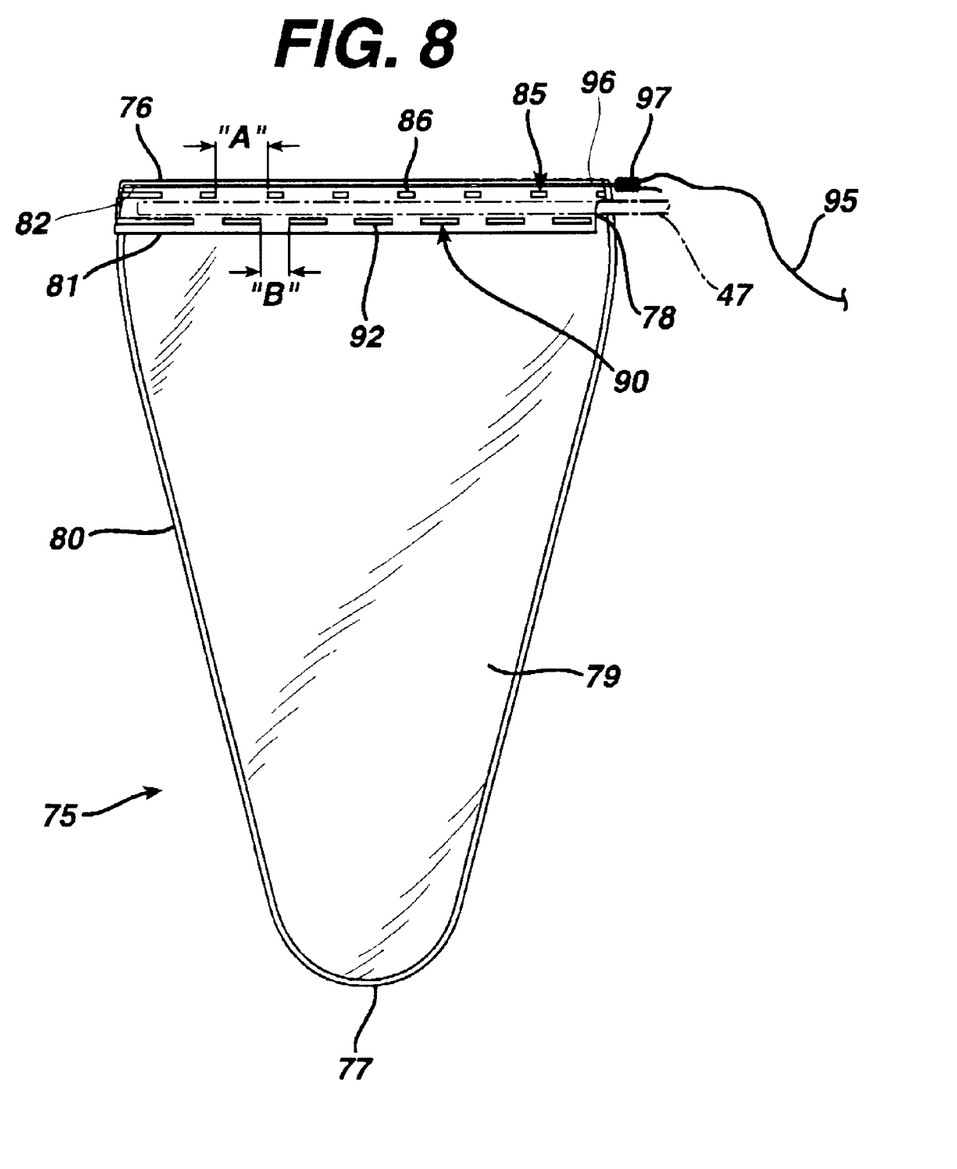
FIG. 8 illustrates a side view of the improved specimen retrieval bag of FIG. 2 having an open end and a closed end and a closure noose, the improved specimen bag having two intermittent weld lines at the open end to enhance the closure of the specimen retrieval bag.
Figure 9:
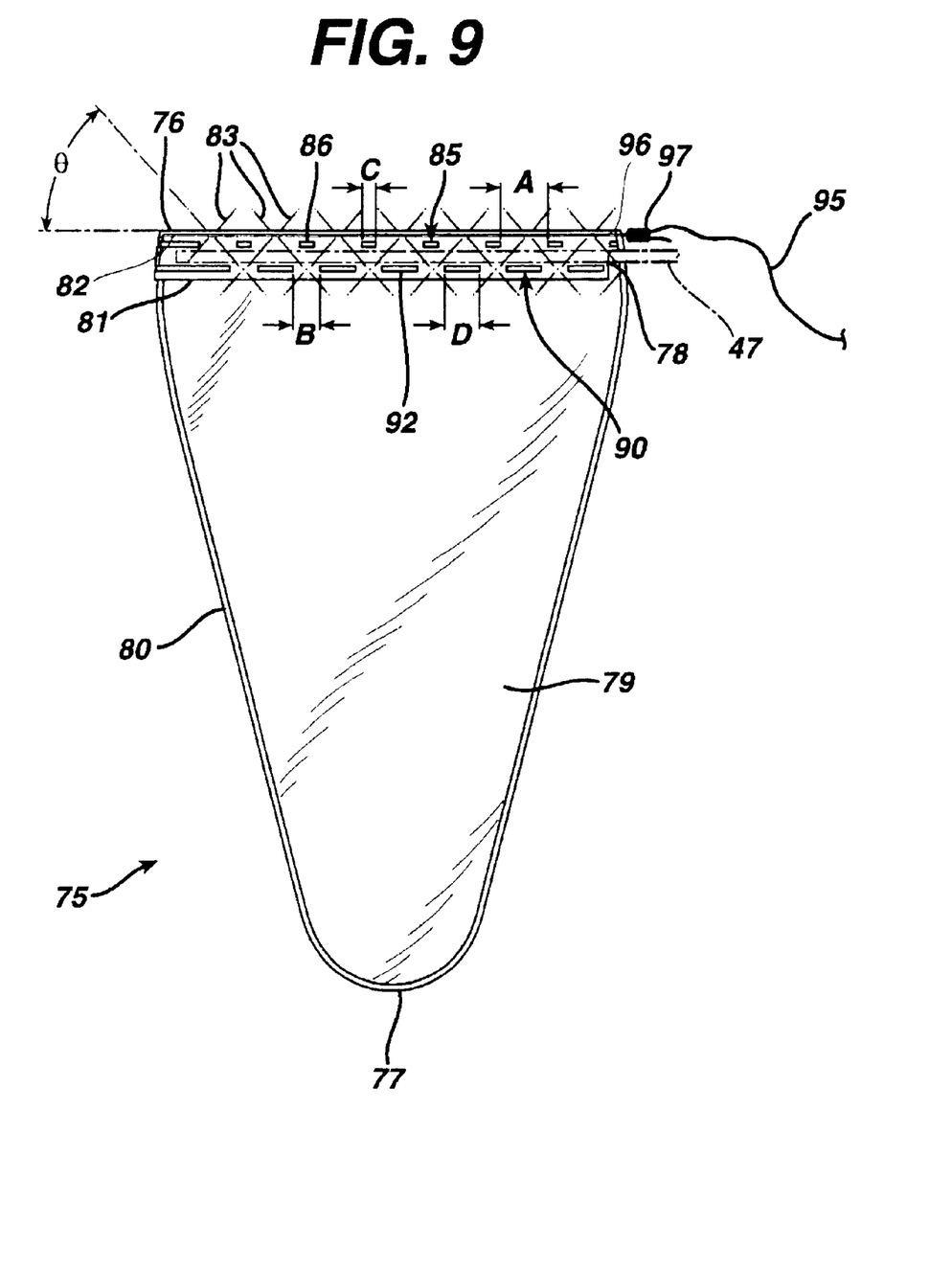
FIG. 9 illustrates a second side view of the specimen retrieval bag of FIG. 2 including diagonal lines between the two intermittent weld lines, the diagonal lines representing the pleat fold lines between the pleat introducers.

FIGS. 8 and 9 illustrate side views of the improved specimen retrieval bag 75, initially shown in FIG. 2 as deployed from the specimen retrieval instrument 20. Improved specimen retrieval bag 75 is generally similar in design and function to the prior art specimen retrieval bag 175, but offers some significant improvements over the prior art bag. Many of the features of the improved specimen retrieval bag 75 are identical to those of the prior art bag 175, but will be given different element numbers for clarity. Improved specimen retrieval bag 75 differs from the prior art in the area around the open end 76 and in the way that the bag closes.

As shown, the improved specimen retrieval bag 75 also has an open end 76, a closed end 77 and a closure mechanism such as closure string 95. Like the prior art retrieval bag 175, the improved specimen retrieval bag 75 can be initially constructed from the same materials and processes described above. That is, the joining of two flat sheets with glue, heat welding, or ultrasonically welding along the sides 80 and closed end 77 to make a bag.

Closure string 95 can be identical to that used by the prior art retrieval bag 175 and is captured at the open end 76 of the improved retrieval bag 75 by folding over a portion of the open end of wall 79 to create a fold wall 81. Circular closure noose 96 is then placed around the improved retrieval bag 75 and slid up into a crotch 82 of the fold between the interior surface of the fold wall 81 and the exterior surface of the bag wall 79. Unlike the prior art retrieval bag 175, the fold wall 81 is attached to exterior wall 79 of the bag in a different manner to provide improved benefits to the user. Carefully staggered intermittent attachment points or first intermittent welds 86 on the improved retrieval bag 75 replace the continuous welds used by prior art retrieval bag 175. Thus, in FIG. 8, the noose 96 is secured around the open end 76 by a first intermittent weld line 85. A second intermittent weld line 90 is formed from spaced apart second intermittent weld areas 92 and form channels 78 on both sides of the bag between the first and second intermittent weld lines 85, 90. The welded areas of the first and second intermittent weld lines 85, 90 are stiffer than the surrounding wall 79 as they are composed of two layers of wall 79 that are bonded together. Additionally, the welded areas and can be embossed or raised outwardly from the surface of the bag from the heat staking or welding process. The channels 78 are provided to receive spring arms 47 and to removable hold the improved specimen retrieval bag 75 on the push/pull rod 45.

The intermittent welds on the first and second intermittent weld lines 85 and 90 are spaced apart by sections of unattached material. The spacing between the first intermittent weld areas 86 is defined by a length "A", and the spacing between the second intermittent welds is defined by a length "B". The "A" spacing is preferably larger than the "B" spacing. The first intermittent weld areas 86 are staggered horizontally relative to the second intermittent weld areas 92 (FIG. 8 and 9).

Intermittent weld lines 85, 90 offer enhanced closure of the improved retrieval bag 75 because they offer alternating areas of stiff (welded) and less stiff (unwelded) wall 79. It is well known phenomenon that when loaded, a less stiff area will buckle or deform before a stiffer area. With proper design, this tendency can be used to enhance the closure of the improved specimen retrieval bag 75 by forcing the bag to buckle or fold in a desired manner as it closes.

Looking at the first intermittent weld line 85, intermittent weld line 85 is composed of alternating first intermittent weld areas 86 and unattached areas or lengths "A". As noose 96 closes, the unattached lengths "A" will buckle or bunch before the intermittent weld areas 86. The spacing of length "A" is maximized between the first intermittent weld areas 86 in the first intermittent weld line 85 to allow the maximum amount of unattached material to easily buckle or bunch between the welds as the noose 96 is tightened. This reduces the force to close, and minimize the size of the closed open end 76. The unattached material "A" between the first intermittent weld areas 86 buckle first, and the stiffer first intermittent welded areas 86 buckle second. Thus, the alternating areas of intermittent weld areas 86 and unattached areas or lengths "A" within the first intermittent weld lines offer alternating zones of controlled buckling during closure. The alternating zones of controlled buckling provide uniformity during the closure process and reduce uneven closure caused by localized bunching. The above reasons enable the first intermittent weld line 85 to be closed tighter than the second intermittent weld line 90 and enhances the closure of the bag.

The second intermittent weld line 90 is also composed of alternating areas of weld defined by second intermittent weld areas 92, and unattached areas defined by the unattached lengths "B". The lengths "B" of unattached wall material are minimized in the second intermittent weld line 90 and are staggered to reside directly below the first weld areas. This is done to produce controlled buckling and folding within the improved specimen retrieval bag 75 as it closes. As shown in FIG. 9, this effect can be used to produce fold lines such as diagonal fold lines 83 that induce pleats (along the diagonal fold lines 83) in the wall 79 of the improved specimen retrieval bag 75 as it is drawn closed. The induced pleats provide uniformity of closure, reduce the size of the closed open end 76 and make it easier to remove the filled improved specimen retrieval bag 75 from the patient. A fold angle θ between the diagonal fold lines 83 and the open end 76 could be between about 1 degree and between about 90 degrees.

Whereas intermittent welds are used in the present invention to induce controlled buckling and folding, other mechanisms can be employed. That is, alternating areas of increased and lessened stiffness are used to force the improved specimen retrieval bag 75 to fold as it closes. Whereas welds and raised sections are used to increase stiffness in localized areas, many alternate embodiments are available. For example, alternating areas of increasing thickness and reduced thickness can produce the same effect. Examples of other embodiments or combinations of embodiments that can accomplish this desired effect are: attachment of rigid or semi-rigid sections of materials such as plastic features onto the improved specimen retrieval bag 75, the use of stiff glues to attach the fold wall 81 onto the pouch, the embossment of stiffening features onto the improved specimen retrieval bag 75, wall sections of different durometer, or the pre-placement of folds in the specimen retrieval bag with heat and pressure (similar to ironing pleats into a women's skirts). Several alternate embodiments are listed, but here are many more embodiments that can accomplish the same goals.

Surgical Procedure Using a Specimen Retrieval Instrument (Not Shown)

Specimen retrieval instruments 20 are frequently used during a cholecystectomy or gall bladder removal. During this endoscopic surgical procedure, the surgeon sedates the patient and insufflates the patient's abdomen with carbon dioxide gas. Next, a series of endoscopic access ports or trocars are placed into the patient's inflated abdomen for the passage of endoscopic instruments therein. The surgeon places a viewing device or endoscope into the patient to visualize the gall bladder and surgical site on a monitor. By viewing the monitor, the surgeon is able to identify, clip, and cut the cystic duct and cystic artery. Next, the gall bladder is carefully removed from the bed of the liver and held in a surgical grasping instrument. An un-actuated specimen retrieval instrument 20 (FIG. 1) is inserted into one of the trocar access ports to retrieve the excised tissue.

Placing his thumb into the thumb ring 46 and index and second fingers into the finger loops 31, the surgeon begins to eject the improved specimen retrieval bag from the specimen retrieval instrument by pushing the thumb ring into the specimen retrieval instrument 20. As the improved specimen retrieval bag 75 is ejected from the support tube, the spring arms 47 began to spread and to open the open end 76 of the bag. During the ejection process, the surgeon inadvertently attempts to pull the thumb ring 46 and push/pull rod 45 from the instrument, but is prevented by the one way ratchet mechanism 55. Once the improved specimen retrieval bag 75 is fully ejected from the support tube 25 (FIG. 2), the one way ratchet mechanism 55 is permanently disabled and proximal and distal movement of the push/pull rod 45 is possible.

The surgeon then places the excised gall bladder into the open end 76 of the improved specimen retrieval bag with a grasping instrument and releases it. Next, the surgeon simultaneously closes the improved specimen retrieval bag 75 around the excised gall bladder and releases it from the spring arms 47 by pulling the thumb ring 46 and push pull rod 45 proximally out of the support tube 25 and handle 30. As the push/pull rod 45 is pulled, the spring arms are pulled proximally from the channels 78 within the improved specimen retrieval bag 75, the closure string 95 is pulled through the slipknot 97 to close the noose 96, and a free end of the closure string 95 is exposed. Slipknot 97 is prevented from moving proximally by the cinching plug 27. As the improved specimen retrieval bag 75 is closed, the intermittent welding on the first and second intermittent weld lines 85, 90 ensures uniform closure of the bag. Angular fold lines 83 form in the less rigid portions of the wall 79 and induce pleats into the bag as it closes and provide improved, consistent bag closure. Once the improved specimen retrieval bag 75 is detached from the spring arms 47, the improved specimen retrieval bag remains attached to the specimen retrieval instrument 20 by closure string 95. The free end of the closure string 95 is easily detached from the push/pull rod outside of the patient. As the specimen retrieval instrument 20 is withdrawn from the patient from the trocar, the closure string 95 is pulled out of the support tube 25.

To remove the filled improved specimen retrieval bag 75 from the patient, the surgeon pulls on the closure string 95 to draw the pleated and closed open end 76 of the filled improved specimen retrieval bag 75 into the cannula of the trocar. While maintaining tension on the closure string 95, the trocar and attached filled improved specimen retrieval bag 75 are pulled from the patient through the trocar incision.

It will be recognized that equivalent structures may be substituted for the structures illustrated and described herein and that the described embodiment of the invention is not the only structure which may be employed to implement the claimed invention. As one example of an equivalent structure which may be used to implement the present invention, such as the attachment of rigid or semi-rigid materials to the wall of the surgical retrieval pouch to produce alternating areas of stiffness and less-stiffness. As a further example of an equivalent structure which may be used to implement the present invention, alternating areas of different durometers may be used. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument for retrieving tissue from a patient, the surgical instrument comprising:
   a. an elongated support tube having a proximal end and a distal end;
   b. an elongated inner rod slidably and coaxially disposed within said support tube, said rod having a removable pouch attached thereto, wherein said pouch is initially disposed within said support tube, and wherein distal movement of said rod ejects said pouch from said tube; and
   c. a mechanism engaging said rod such that after said rod has initially been moved distally, such mechanism prevents proximal motion of said rod, said mechanism disengaging upon total ejection of said bag from said tube, and thereafter allowing proximal and distal movement of said rod.

2. The surgical instrument of claim 1 wherein said motion limiting mechanism is a one way ratchet.

3. The surgical instrument of claim 2 wherein said one way ratchet includes a longitudinal row of pockets disposed along said rod and at least one arm biased against said female features.

4. The surgical instrument of claim 3 wherein said arm is biased against said pockets by a spring.

5. The surgical instrument of claim 1 wherein said locking mechanism is a hook.

6. A surgical instrument for retrieving tissue from a patient, the surgical instrument comprising:
   a. an elongated support tube having a proximal end attached to a handle and a distal end extending therefrom;
   b. an elongated inner rod slidably and coaxially disposed within said support tube, said rod having a removable pouch attached thereto, wherein said pouch is initially disposed within said support tube, and wherein distal movement of said rod ejects said pouch from said tube; and
   c. a mechanism engaging said rod such that after said rod has initially been moved distally, such mechanism prevents proximal motion of said rod, said mechanism disengaging upon total ejection of said bag from said tube, and thereafter allowing proximal and distal movement of said rod, said mechanism engaging said rod remaining substantially stationary with respect to said handle.

7. The surgical instrument of claim 6 wherein said motion limiting mechanism is a one way ratchet.

8. The surgical instrument of claim 7 wherein said one way ratchet includes a longitudinal row of pockets disposed along said rod and at least one arm biased against said female features.

9. The surgical instrument of claim 8 wherein said arm is biased against said pockets by a spring.

10. The surgical instrument of claim 6 wherein said locking mechanism is a hook.

* * * * *